(12) United States Patent
Davis et al.

(10) Patent No.: US 7,557,198 B2
(45) Date of Patent: Jul. 7, 2009

(54) ACUTE MYELOGENOUS LEUKEMIA BIOMARKERS

(75) Inventors: Lisa Davis, Albuquerque, NM (US); Cole Harris, Houston, TX (US)

(73) Assignee: Exagen Diagnostics, Inc., Albuquerque, NM (US)

( * ) Notice: Subject to any disclaimer, the term of this patent is extended or adjusted under 35 U.S.C. 154(b) by 0 days.

(21) Appl. No.: 11/417,450

(22) Filed: May 3, 2006

(65) Prior Publication Data

US 2006/0281107 A1 Dec. 14, 2006

Related U.S. Application Data

(60) Provisional application No. 60/677,765, filed on May 4, 2005.

(51) Int. Cl.
*C07H 21/02* (2006.01)
(52) U.S. Cl. .................................... 536/23.1
(58) Field of Classification Search ................. 536/23.1
See application file for complete search history.

(56) References Cited

U.S. PATENT DOCUMENTS

| | | | |
|---|---|---|---|
| 5,750,340 A | 5/1998 | Kim et al. | |
| 6,022,689 A | 2/2000 | Sarto et al. | |
| 6,664,057 B2 | 12/2003 | Albertson et al. | |
| 7,171,311 B2 * | 1/2007 | Dai et al. | 702/19 |
| 2002/0156263 A1 * | 10/2002 | Chen | 536/23.2 |
| 2003/0187584 A1 | 10/2003 | Harris et al. | |
| 2004/0005644 A1 * | 1/2004 | Su et al. | 435/7.23 |

FOREIGN PATENT DOCUMENTS

| | | |
|---|---|---|
| WO | WO 96/17958 | 6/1996 |
| WO | WO 03/073911 A2 * | 9/2003 |
| WO | 03083760 | 10/2003 |
| WO | WO 03/102235 | 12/2003 |

OTHER PUBLICATIONS

Valk et al., New England J of Medicine, 350(16):1617-1628.
Bullinger et al., New England J. of Medicine, 350(16):1605-1616 (2004).
Genbank Accession NM_021961.
Genbank Accession BX537894.
Genbank Accession NM_000090.
Genbank Accession X00588.
Genbank Accession X63556.
Genbank Accession AK074614.
Genbank Accession NM_175767.
Genbank Accession X07173.
Genbank Accession BC042897.
Genbank Accession BC009831.
Genbank Accession BC009361.
Genbank Accession BC036503.
Genbank Accession X78565.
Strauss-Soukup (1997) Biochemistry 36:8692-8698.
Milligan (1993) J. Med. Chem. 36:1923-1937; Antisense Research and Applications (1993, CRC Press).
Pearson (1983) J. Chrom. 255:137-149.
Tijssen (1993) Laboratory Techniques in Biochemistry and Molecular Biology-Hybridization with Nucleic Acid Probes part I, chapter 2, "Overview of principles of hybridization and the strategy of nucleic acid probe assays," Elsevier, N.Y.
Pastinen (1997) Genome Res. 7:606-614.
Wan (1996) Nature Biotechnology 14:1685.
Chee (1996) Science 274:610.
Alvarez, et al. (2001) Genes Chromosomes and Cancer 32(3): 285-293.
Schoch, et al. (2004) Blood 104(11): 556A.
Walter, et al. (2004) Blood 104(11): 44A.
Walter, et al. (2005) Blood 106(11): 661A.
Schoch, et al. (2002) Proceedings of the National Academy of Sciences of USA 99(15):10008-10013.
Kohlmann, et al. (2003) Genes, Chromosomes, and Cancer 37(4): 396-405.
Schoch, et al. "Specific abnormalities on the genomic level result in a distinct gene expression pattern detected by oligonucleotide microarrays: An analysis of 25 patients with AML M2/t(8)" Biosis, Nov. 2001.
Haferlach, et al. "Gene expression profiling is able to reproduce difference phenotypes in AML as defined by the FAB classification," Biosis, Nov. 2002.
Haferlach, et al., "Genetic profiling in acute monblastic versus acute moncytic leukemia: A gene expression study on 22 patients," Biosis, Nov. 2002.
http://genome.ucsc.edu/index.html?org=Human.
http://genome.ucsc.edu/cgi-bin/hgTracks.

* cited by examiner

*Primary Examiner*—Sean E Aeder
(74) *Attorney, Agent, or Firm*—McDonnell Boehnen Hulbert & Berghoff LLP

(57) ABSTRACT

The present invention provides novel compositions and their use in classifying acute myelogenous leukemia.

10 Claims, 4 Drawing Sheets

FIGURE 1A

| Unigen Hs.# gets to mRNA | length of mRNA | Gene Name | alternate name | chromosome | BAC ID | BAC start | BAC finish | BAC size |
|---|---|---|---|---|---|---|---|---|
| NM_021961 1 (SEQ ID:1) | 8850bp | TEAD1 | | 11p15.2 | RP11-599L08 (SEQ ID: 14) | 12864564 | 13039514 | 174950 |
| | | | | | RP11-756C18 (15) | 12982506 | 13132900 | 150394 |
| BX537894 2 (SEQ ID:2) | 3425 bp | | similar to glutathione peroxidase 2 | 5q11.2 | RP11-101I03 (SEQ ID: 16) | 54373904 | 54525704 | 151800 |
| NM_000090 3 (SEQ ID:3) | 5489 bp | COL3A1 | Ehlers-Danlos | 2q32.2 | RP11-622E16 (SEQ ID: 17) | 189723172 | 189897778 | 174606 |
| | | | | | RP11-634B17 (18) | 189794106 | 189976619 | 182513 |
| | | | | | RP11-1151E08 (SEQ ID: 19) | 189801124 | 189961814 | 160690 |
| X00588 (SEQ ID:4) | 5532 bp | EGFR | v-erb-b | 7p11.2 | RP11-781C22 (SEQ ID: 20) | 54695719 | 54871777 | 176058 |
| | | | | | CTD-2026N22 (SEQ ID: 21) | 54829802 | 54980210 | 150408 |
| | | | | | RP11-708P05 (SEQ ID: 22) | 54968643 | 55127566 | 158923 |
| | | | | | RP11-42K15 (SEQ ID: 23) | 46264960 | 46428008 | 163048 |
| | | | | | RP11-7J12 (SEQ ID: 24) | 46411271 | 46552128 | 140857 |
| X63556 (SEQ ID:5) | 9940 bp | FBN1 | Marfan Syndrome | 15q21.1 | RP11-348A14 (SEQ ID: 25) | 46141862 | 46333908 | 192046 |
| AK074614 6 (SEQ ID:6) | 2159 bp | putative IGF2 associated protein | hypothetical protein AK074614 | 11p15.5 | RP11-200C14 (SEQ ID: 26) | 2058679 | 2224682 | 166003 |
| | | | | | RP11-650O21 (SEQ ID: 27) | 2060017 | 2248425 | 188408 |
| | | | | | RP11-395G19 (SEQ ID: 28) | 55072048 | 55269120 | 197072 |
| | | | | | RP11-806P19 (SEQ ID: 29) | 55134284 | 55314795 | 180511 |
| | | | | | RP11-239D15 (SEQ ID: 30) | 55185675 | 55346158 | 160483 |
| NM_175767 7 (SEQ ID:7) | 3159 bp | IL6ST | gp130 Oncostatin M | 5q11.2 | RP11-321M06 (SEQ ID: 31) | 54999260 | 55218231 | 218971 |

FIGURE 1B

| | | | | | | |
|---|---|---|---|---|---|---|
| 8 | X07173 (SEQ ID:8) | 3089 bp | ITIH2 | | RP11-454I03 (SEQ ID: 32) | 7797933 | 7948167 | 150234 |
| 9 | BC042897 (SEQ ID:9) | 3049 bp | NR2F2 | 10p14 | RP11-45N19 (SEQ ID: 33) | 7866929 | 8041466 | 174537 |
| 10 | BC009831 (SEQ ID:10) | 1101 bp | RAB 25 | 15q26.2 | RP11-163P10 (SEQ ID: 34) | 94333052 | 94483707 | 150655 |
| | | | | 1q22 | RP11-702H12 (SEQ ID: 35) | 152759070 | 152923486 | 164416 |
| | | | | | RP11-714M16 (SEQ ID: 36) | 121229505 | 121423140 | 193635 |
| 11 | BC009361 (SEQ ID:11) | 769 bp | RGS10 | | RP11-278I18 (SEQ ID: 37) | 121363407 | 121528619 | 165212 |
| | | | | 10q26.11 | RP11-420N23 (SEQ ID: 38) | 121371833 | 121460477 | 88644 |
| 12 | BC036503 (SEQ ID:12) | 4482 bp | SFRP1 | 8p11.21 | RP11-11B23 (SEQ ID: 39) | 40821363 | 40955762 | 134399 |
| | | | | | RP11-818J03 (SEQ ID: 40) | 111155244 | 111327811 | 172567 |
| 13 | X78565 (SEQ ID:13) | 7560 bp | TNC | 9q32 | RP11-472E10 (SEQ ID: 41) | 111315127 | 111465510 | 150383 |

FIGURE 2A

| Significant 3-gene markers (p<=.05) gene | | | training data | | | | bootstrap | | | | test data | | | |
|---|---|---|---|---|---|---|---|---|---|---|---|---|---|---|
| A | B | C | misclassified | total poor outcome | misclassified | good outcome | misclassified | total poor outcome | good outcome misclassified | good outcome | poor outcome misclassified | total poor outcome | good outcome misclassified | total good outcome |
| sGPX2 | SFRP1 | ITIH2 | 4 | 23 | 0 | 10 | 243 | 993 | 45 | 407 | 1 | 8 | 1 | 4 |
| sGP2 | COL3A1 | FBN1 | 3 | 23 | 1 | 10 | 141 | 979 | 69 | 421 | 1 | 8 | 2 | 4 |
| TNC | sGPX2 | SFRP1 | 4 | 23 | 0 | 10 | 234 | 992 | 31 | 408 | 0 | 8 | 1 | 4 |
| RGS10 | sGPX2 | SFRP1 | 4 | 23 | 0 | 10 | 196 | 961 | 45 | 439 | 2 | 8 | 1 | 4 |
| TNC | IL6ST | sGPX2 | 4 | 23 | 1 | 10 | 191 | 997 | 136 | 403 | 0 | 8 | 2 | 4 |
| TNC | SFRP1 | ITIH2 | 7 | 23 | 0 | 10 | 318 | 982 | 69 | 418 | 0 | 8 | 0 | 4 |
| sGPX2 | ITIH2 | FBN1 | 1 | 23 | 3 | 10 | 245 | 971 | 105 | 429 | 0 | 8 | 2 | 4 |
| TNC | pIGF2AP | SFRP1 | 6 | 23 | 0 | 10 | 291 | 964 | 48 | 436 | 0 | 8 | 0 | 4 |
| pIGF2AP | sGPX2 | COL3A1 | 8 | 23 | 0 | 10 | 263 | 971 | 95 | 429 | 2 | 8 | 1 | 4 |
| sGPX2 | SFRP1 | COL3A1 | 4 | 23 | 1 | 10 | 223 | 991 | 90 | 409 | 2 | 8 | 1 | 4 |
| pIGF2AP | sGPX2 | SFRP1 | 7 | 23 | 0 | 10 | 328 | 971 | 42 | 429 | 0 | 8 | 1 | 4 |
| pIGF2AP | sGPX2 | ITIH2 | 7 | 23 | 0 | 10 | 316 | 969 | 60 | 431 | 2 | 8 | 1 | 4 |
| IL6ST | ITIH2 | FBN1 | 1 | 23 | 3 | 10 | 82 | 982 | 172 | 418 | 1 | 8 | 2 | 4 |
| TNC | sGPX2 | ITIH2 | 4 | 23 | 1 | 10 | 265 | 993 | 82 | 407 | 0 | 8 | 1 | 4 |
| sGPX2 | SFRP1 | FBN1 | 8 | 23 | 0 | 10 | 304 | 987 | 116 | 413 | 3 | 8 | 0 | 4 |
| TNC | SFRP1 | COL3A1 | 4 | 23 | 1 | 10 | 231 | 988 | 112 | 412 | 0 | 8 | 1 | 4 |
| sGPX2 | SFRP1 | RAB25 | 3 | 23 | 0 | 10 | 312 | 975 | 46 | 425 | 0 | 8 | 2 | 4 |
| EGFR | sGPX2 | ITIH2 | 8 | 23 | 1 | 10 | 352 | 978 | 79 | 422 | 1 | 8 | 1 | 4 |
| EGFR | sGPX2 | FBN1 | 4 | 23 | 1 | 10 | 228 | 974 | 147 | 426 | 2 | 8 | 1 | 4 |
| SFRP1 | COL3A1 | RAB25 | 3 | 23 | 1 | 10 | 150 | 987 | 84 | 413 | 0 | 8 | 1 | 4 |
| TNC | EGFR | ITIH2 | 4 | 23 | 0 | 10 | 224 | 995 | 103 | 405 | 0 | 8 | 1 | 4 |
| RGS10 | pIGF2AP | sGPX2 | 6 | 23 | 3 | 10 | 279 | 983 | 57 | 417 | 3 | 8 | 2 | 4 |
| IL6ST | SFRP1 | FBN1 | 1 | 23 | 2 | 10 | 145 | 951 | 202 | 449 | 0 | 8 | 1 | 4 |
| sGPX2 | ITIH2 | COL3A1 | 4 | 23 | 1 | 10 | 280 | 985 | 91 | 415 | 2 | 8 | 0 | 4 |
| pIGF2AP | ITIH2 | COL3A1 | 7 | 23 | 1 | 10 | 314 | 978 | 123 | 422 | 1 | 8 | 0 | 4 |
| TNC | IL6ST | EGFR | 6 | 23 | 1 | 10 | 219 | 991 | 122 | 409 | 1 | 8 | 0 | 4 |

FIGURE 2B

| | | | | | | | | | | | |
|---|---|---|---|---|---|---|---|---|---|---|---|
| TNC | RGS10 | SFRP1 | 3 | 23 | 2 | 10 | 302 | 931 | 112 | 469 | 0 | 8 | 1 | 4 |
| sGPX2 | SFRP1 | TEAD1 | 6 | 23 | 0 | 10 | 266 | 1003 | 78 | 397 | 1 | 8 | 2 | 4 |
| ITIH2 | RAB25 | FBN1 | 5 | 23 | 1 | 10 | 228 | 955 | 133 | 445 | 3 | 8 | 1 | 4 |
| pIGF2AP | SFRP1 | ITIH2 | 7 | 23 | 1 | 10 | 351 | 972 | 79 | 428 | 0 | 8 | 0 | 4 |
| EGFR | SFRP1 | COL3A1 | 4 | 23 | 1 | 10 | 301 | 990 | 72 | 410 | 1 | 8 | 1 | 4 |
| TNC | EGFR | sGPX2 | 3 | 23 | 2 | 10 | 248 | 968 | 121 | 432 | 0 | 8 | 1 | 4 |
| IL6ST | pIGF2AP | ITIH2 | 2 | 23 | 3 | 10 | 124 | 982 | 173 | 418 | 0 | 8 | 2 | 4 |
| TNC | ITIH2 | FBN1 | 3 | 23 | 2 | 10 | 236 | 979 | 129 | 421 | 2 | 8 | 1 | 4 |
| pIGF2AP | EGFR | SFRP1 | 8 | 23 | 0 | 10 | 356 | 992 | 77 | 408 | 1 | 8 | 0 | 4 |
| TNC | EGFR | TEAD1 | 4 | 23 | 1 | 10 | 202 | 952 | 126 | 448 | 0 | 8 | 2 | 4 |
| SFRP1 | ITIH2 | COL3A1 | 4 | 23 | 2 | 10 | 252 | 980 | 130 | 420 | 0 | 8 | 3 | 4 |
| RGS10 | SFRP1 | ITIH2 | 8 | 23 | 0 | 10 | 325 | 982 | 66 | 418 | 3 | 8 | 0 | 4 |
| EGFR | sGPX2 | TEAD1 | 5 | 23 | 1 | 10 | 379 | 974 | 78 | 426 | 1 | 8 | 2 | 4 |
| pIGF2AP | sGPX2 | NR2F2 | 2 | 23 | 2 | 10 | 175 | 969 | 141 | 431 | 0 | 8 | 3 | 4 |
| SFRP1 | ITIH2 | FBN1 | 8 | 23 | 1 | 10 | 322 | 983 | 149 | 417 | 2 | 8 | 0 | 4 |
| pIGF2AP | SFRP1 | TEAD1 | 2 | 23 | 3 | 10 | 276 | 971 | 136 | 429 | 0 | 8 | 2 | 4 |

ACUTE MYELOGENOUS LEUKEMIA BIOMARKERS

CROSS REFERENCE

This application claims priority to U.S. Patent Application Ser. No. 60/677,765 filed May 4, 2005, incorporated by reference herein in its entirety.

Sequence Listing

The sequence listing submitted on compact disc, in compliance with 37 C.F.R. § 1.52(e)(5), in incorporated by reference. Two separate compact discs are submitted, each containing the file "05-116.SeqList" (5,951,488 bytes in size on disk), each created on CD on May 3, 2006.

BACKGROUND

Acute myeloid leukemia (AML), also called acute non-lymphocytic, granulocytic, myelocytic, myeloblastic, or myeloid leukemia, is a disease in which cancer cells develop in the blood and bone marrow. The cancer develops from two main types of immature white blood cells that normally develop into mature granulocytes or monocytes. The result is a malignancy characterized by the accumulation in blood and bone marrow of abnormal hematopoietic progenitors and disruption of normal production of erythroid, myeloid, and/or megakaryocytic cell lines. It can be subdivided morphologically into specific types depending on which cell lines are involved. AML subtypes (M0-M7) are determined by cell morphology with particular subtypes such as M3 (acute promyelocytic leukemia or APL) having a more favorable outcome:

M0: undifferentiated large granular;
M1 and M2: acute myeloblastic;
M3: acute promyelocytic;
M4: myelomonocytic;
M5: monocytic;
M6: erythroleukemia;
M7: megakaryocytic; and
M4Eo: eosinphils.

By classifying AML in this manner, developed treatments can more specifically eradicate the particular defective cell clone and hopefully provide a better outcome after therapy. However, the leukemia cell karyotype is more relevant for determination of appropriate therapeutic options.

Current AML therapy regimens generally involve two stages: Initial treatment ("induction therapy") for AML is aimed at eradicating the leukemic clone to re-establish normal hematopoiesis, and post-remission therapy. AML treatment generally involves chemotherapy, and sometimes involves radiation therapy to relieve AML-induced bone pain. For patients who have relapses or have AML that does not respond to other treatment, bone marrow transplantation ("BMT") may be required, and can often increase survival.

Certain chromosomal abnormalities are routinely used to determine prognosis in adult AML patients, including t(8;21), t(15;17) or inv(16) suggestive of better prognosis; t(9; 11) used to classify patients at intermediate risk; and inv(3), −5/del(5q), −7/del(7q), t(6;9), abnormalities involving 11q23, or a complex karyotype (three or more cytogenetic aberrations) used to classify patient as being at high risk (Valk et al., New England J of Medicine, 350(16):1617-1628; Bullinger et al., New England J. of Medicine, 350(16):1605-1616 (2004)). However a significant proportion of AML patients do not exhibit such genetic abnormalities. These patients are termed the "normal karyotype" subset of AML patients, and there is currently no consensus for either risk stratification or optimal treatment regimen for this group. A means to provide a prognosis for these patients would likely be of great clinical utility.

SUMMARY OF THE INVENTION

In a first aspect, the present invention provides compositions comprising an AML biomarker, wherein the AML biomarker consists of between 2 and 60 different probe sets, wherein at least 20% of the different probe sets comprise one or more isolated polynucleotides that selectively hybridize to a genomic region selected from the group consisting of 11p15.2; 5q11.2;2q32.2;7p11.2; 15q21.1; 11p15.5; 10p14; 15q26.2; 1q22; 10q26.11; 8p11.21; and 9q32;wherein the different probe sets in total selectively hybridize to at least two of the recited genomic regions.

In a second aspect, the present invention provides compositions comprising an AML biomarker consisting of between 2 and 65 different probe sets, wherein at least 20% of the different probe sets comprise one or more isolated polynucleotides that selectively hybridize to a nucleic acid according to formula 1, or complements thereof:

X1-X2-X3;

wherein X2 is a human genomic insert contained within a bacterial artificial chromosome ("BAC") selected from the group consisting of SEQ ID NOS:14-41, wherein X1 and X3 are independently 0-500 kB of human genomic nucleic acid flanking X2 in the human genome; and wherein the different polynucleotide probe sets in total selectively hybridize to at least two non-overlapping polynucleotides according to formula 1, or complements thereof.

In a third aspect, the present invention provides compositions comprising an AML biomarker consisting of between 2 and 65 different probe sets, wherein at least 20% of the different probe sets comprise one or more isolated polynucleotides that selectively hybridize to a nucleic acid sequence according to one of SEQ ID NOS:1-13 or complements thereof; wherein the different probe sets in total selectively hybridize to at least two of the recited nucleic acid sequences according to SEQ ID NOS:1-13 or complements thereof.

In a further aspect, the present invention provides methods for classifying AML in a patient, comprising (a) contacting a nucleic acid sample obtained from a subject having AML with polynucleotide probes that, in total, selectively hybridize to two or more genomic regions selected from the group consisting of 11p15.2; 5q11.2; 2q32.2; 7p11.2; 15q21.1; 11p15.5; 10p14; 15q26.2; 1q22; 10q26.11; 8p11.21; and 9q32; wherein the contacting occurs under conditions to promote selective hybridization of the polynucleotides of the probe set to the two or more genomic regions;

(b) detecting formation of hybridization complexes;

(c) determining whether one or more of the genomic regions are present in an altered copy number in the nucleic acid sample; and (d) correlating an altered copy number of one or more of the genomic regions with an AML classification.

In a still further aspect, the present invention provides methods for classifying AML comprising:

(a) contacting a mRNA-derived nucleic acid sample obtained from a subject having AML with nucleic acid probes that, in total, selectively hybridize to two or more nucleic acid targets selected from the group consisting of SEQ ID NO:1-13 or complements thereof; wherein the contacting occurs under conditions to promote selective hybridization of the nucleic acid probes to the nucleic acid targets, or complements thereof, present in the nucleic acid sample;

(b) detecting formation of hybridization complexes between the nucleic acid probes to the nucleic acid targets, or complements thereof, wherein a number of such hybridization complexes provides a measure of gene expression of the one or more nucleic acids according to SEQ ID NO:1-13; and (c) correlating an alteration in gene expression of the one or more nucleic acids according to SEQ ID NO:1-13 relative to control with an AML classification.

In a further aspect, the present invention provides kits comprising a composition of the invention and a set of instructions for using the composition for AML classification.

BRIEF DESCRIPTION OF THE FIGURES

FIGS. 1a and 1b is a spreadsheet summary of individual markers, their GenBank accession number, Unigene numbers, genomic region at which the genes are located, and the names of bacterial artificial chromosomes ("BAC") that contain the gene.

FIGS. 2a and 2b is a spreadsheet of two-gene and three-gene signatures correlating with AML prognosis in a publicly available gene expression dataset.

DETAILED DESCRIPTION OF THE INVENTION

All publications, GenBank Accession references, references to bacterial artificial chromosome ("BAC") accession numbers (sequences), patents and patent applications cited herein are hereby expressly incorporated by reference for all purposes.

Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique*, 2$^{nd}$ Ed. (R. I. Freshney. 1987. Liss, Inc. New York, N.Y.), *Gene Transfer and Expression Protocols*, pp. 109-128, ed. E. J. Murray, The Humana Press Inc., Clifton, N.J.), and the Ambion 1998 Catalog (Ambion, Austin, Tex.).

The present invention provides novel compositions and methods for their use in providing a prognosis for acute myelogenous leukemia patients ("AML"). As used herein, the term "prognosis" means a prediction of the probable course and outcome of the AML, including the following:

(a) Patient prognosis in the absence of therapy (ie: chemotherapy or radiation therapy;
(b) Prognosis of patient response to treatment (chemotherapy, radiation therapy)
(c) Predicted optimal course of treatment for the patient;
(d) Prognosis for patient relapse after treatment, for example, by prognosis of minimal residual disease (such patients have high risk of relapse)
(e) Patient life expectancy.

The compositions of the present invention are defined relative to the following nucleic acid sequences that are identified herein as being useful markers for AML prognosis:

1. GENBANK ACCESSION NM_021961 (SEQ ID NO:1): EST (TEAD1)

2. GENBANK ACCESSION BX537894 (SEQ ID NO:2): similar to glutathione peroxidase 2 ("sGPX2").

3. GENBANK ACCESSION NM_000090 (SEQ ID NO:3): COL3A1 pro-collagen alpha 1(III) chain ("Ehlers-Danlos").

4. GENBANK ACCESSION X00588 (SEQ ID NO:4): EGFR epidermal growth factor receptor precursor (v-erb-b).

5. GENBANK ACCESSION X63556 (SEQ ID NO:5): FBN1 fibrillin 1 precursor ("Marfan Syndrome").

6. GENBANK ACCESSION AK074614 (SEQ ID NO:6): pIGF2AP: Putative insulin-like growth factor II associated protein 7. GENBANK ACCESSION NM_175767 (SEQ ID NO:7): IL6ST interleukin-6 receptor beta chain precursor (gp130; oncostatin M receptor).

8. GENBANK ACCESSION X07173 (SEQ ID NO:8): ITIH2; inter-alpha-trypsin inhibitor complex component II.

9. GENBANK ACCESSION BC042897 (SEQ ID NO:9): NR2F2.

10. GENBANK ACCESSION BC009831 (SEQ ID NO:10): RAB25; ras-related protein.

11. GENBANK ACCESSION BC009361 (SEQ ID NO:11): RGS10; regulator of g-protein signaling.

12. GENBANK ACCESSION BC036503 (SEQ ID NO:12): SFRP1.

13. GENBANK ACCESSION X78565 (SEQ ID NO:13): TNC; tenascin precursor.

While individually predictive, the inventors believe that the clinical prognostic utility of combinations of these and related markers disclosed herein will be greater than the clinical diagnostic utility of individual markers. Such combinations may better classify the complexity of genomic aberrations associated with particular AML phenotypes.

Physical distances between the genes used in these studies, as described in publicly available databases (for example, UCSC human genome web site genome.ucsc.edu) reveals that, while the sizes of amplifications vary among tumors, the size of an "average" amplification is reasonably estimated as at least 1 megabase.

Thus, in a first aspect, the present invention provides compositions comprising or consisting of an AML biomarker, wherein the AML biomarker comprises or consists of between 2 and 60 different probe sets, wherein at least 20% of the different probe sets comprise or consist of one or more isolated polynucleotides that selectively hybridize to a genomic region selected from the group consisting of 11p15.2; 5q11.2; 2q32.2; 7p11.2; 15q21.1; 11p15.5; 10p14; 15q26.2; 1q22; 10q26.11; 8p11.21; and 9q32; wherein the different probe sets in total selectively hybridize to at least two of the recited genomic regions. The term "AML biomarker" as used herein for all of the aspects and embodiments of the invention, refers to its use in classifying AMLs. The recited genomic regions correspond to the chromosome band of the markers, and the compositions of the invention can be used, for example, to provide improved AML prognosis over that possible using prior art diagnostic and predictive compositions and methods. FIG. 1 provides a detailed summary of the individual markers, their GenBank accession number, Unigene numbers, genomic region at which the genes are located, and the names of bacterial artificial chromosomes ("BAC") that contain the gene (discussed in more detail below).

Thus, the compositions of each aspect and embodiment of the present invention are useful, for example, in classifying human AMLs. The compositions can be used, for example, to identify one or more genomic regions as present in an abnormal copy number (for example, more than two copies of the gene per cell in a chromosome spread or fewer than two copies of the gene) in a nucleic acid sample from a human specimen, such as peripheral blood, inflammatory sites, or bone marrow sample from a human AML patient, or in specific cells isolated from such specimens, such as granulocyte precursors, or monocyte precursors, which provides a prognosis of the AML patient as discussed above and below. Alternatively, certain embodiments of the compositions (as discussed in more detail below) are preferred for use in determining the expression levels in tissue of the MRNA encoded by the genes recited above.

The compositions according to each of the aspects and embodiments of the invention provide an improvement over the prior art for AML prognosis, which requires a much larger number of probes to provide a prognosis for an AML patient, and does so with reduced accuracy compared to the AML biomarker of the present invention. As a result, the compositions of the present invention are much more amenable to use in clinical prognostic testing than are prior art methods for AML prognosis.

The term "polynucleotide" as used herein with respect to each aspect and embodiment of the invention refers to DNA or RNA, preferably DNA, in either single- or double-stranded form. It includes the recited sequences as well as their complementary sequences, which will be clearly understood by those of skill in the art. The term "polynucleotide" encompasses nucleic acids containing known analogues of natural nucleotides which have similar or improved binding properties, for the purposes desired, as the disclosed polynucleotides. The term also encompasses nucleic-acid-like structures with synthetic backbones. DNA backbone analogues provided by the invention include phosphodiester, phosphorothioate, phosphorodithioate, methylphosphonate, phosphoramidate, alkyl phosphotriester, sulfamate, 3'-thioacetal, methylene(methylimino), 3'-N-carbamate, morpholino carbamate, and peptide nucleic acids (PNAs), methylphosphonate linkages or alternating methylphosphonate and phosphodiester linkages (Strauss-Soukup (1997) Biochemistry 36:8692-8698), and benzylphosphonate linkages, as discussed in U.S. Pat. No. 6,664,057; see also Oligonucleotides and Analogues, a Practical Approach, edited by F. Eckstein, IRL Press at Oxford University Press (1991); Antisense Strategies, Annals of the New York Academy of Sciences, Volume 600, Eds. Baserga and Denhardt (NYAS 1992); Milligan (1993) J. Med. Chem. 36:1923-1937; Antisense Research and Applications (1993, CRC Press).

An "isolated" polynucleotide as used herein for all of the aspects and embodiments of the invention is one which is free of sequences which naturally flank the polynucleotide in the genomic DNA of the organism from which the nucleic acid is derived, except as specifically described herein. Preferably, an "isolated" polynucleotide is substantially free of other cellular material, gel materials, vector linker sequences, and culture medium when produced by recombinant techniques, or substantially free of chemical precursors or other chemicals when chemically synthesized. The polynucleotides of the invention may be isolated from a variety of sources, such as by PCR amplification from genomic DNA, mRNA, or cDNA libraries derived from mRNA, using standard techniques; or they may be synthesized in vitro, by methods well known to those of skill in the art, as discussed in U.S. Pat. No. 6,664,057 and references disclosed therein. Synthetic polynucleotides can be prepared by a variety of solution or solid phase methods. Detailed descriptions of the procedures for solid phase synthesis of polynucleotide by phosphite-triester, phosphotriester, and H-phosphonate chemistries are widely available. (See, for example, U.S. Pat. No. 6,664,057 and references disclosed therein). Methods to purify polynucleotides include native acrylamide gel electrophoresis, and anion-exchange HPLC, as described in Pearson (1983) J. Chrom. 255:137-149. The synthetic polynucleotide sequences can be verified using standard methods.

As used herein with respect to all aspects and embodiments of the invention, a "probe set" refers to a group of one or more polynucleotides that each selectively hybridize to the same target (for example, a specific genomic region or mRNA) that can be used, for example, in AML classification. Thus, a single "probe set" may comprise any number of different isolated polynucleotides that selectively hybridize to a given target. For example, a probe set that selectively hybridizes to SEQ ID NO:10 may comprise one or more probes for a single 100 nucleotide segment of SEQ ID NO:10 and also a different 100 nucleotide segment of SEQ ID NO:10, or both these in addition to a separate 10 nucleotide segment of SEQ ID NO:10, or 500 different 10 nucleotide segments of SEQ ID NO:10 (such as, for example, fragmenting a larger probe into many individual short polynucleotides). Those of skill in the art will understand that many such permutations are possible.

In this first aspect, the AML biomarker can be any AML biomarker that contains between 2 and 60 probe sets as defined herein, wherein at least 20% of the probe sets comprise or consist of one or more isolated polynucleotides that selectively hybridize to one of the recited genomic regions. Such AML biomarkers thus can contain other probe sets for use in AML prognosis, so long as at least 20% of the probe sets comprise or consist of one or more isolated polynucleotides that selectively hybridize to one of the recited genomic regions, and so long as no more than 60 probe sets are present in the AML biomarker.

In preferred embodiments of the first aspect of the invention, at least 25%, 30%, 35%, 40%, 45%, 50%, 55%, 60%, 65%, 70%, 80%, 85%, 90%, 95%, or 100% of the probe sets comprise or consist of one or more isolated polynucleotides that selectively hybridize to one of the recited genomic regions, and/or that the different probe sets in total selectively hybridize to at least 3, 4, 5, 6, 7, 8, 9, 10, 11, or 12 of the recited genomic regions. As will be apparent to those of skill in the art, as the percentage of probe sets that comprise or consist of one or more isolated polynucleotides that selectively hybridize to one of the recited genomic regions increases, the maximum number of probe sets in the AML biomarker will decrease accordingly. Thus, for example, where at least 50% of the probe sets comprise or consist of one or more isolated polynucleotides that selectively hybridize to one of the recited genomic regions, the AML marker will consist of between 2 and 24 probe sets. Those of skill in the art will recognize the various other permutations encompassed by the compositions according to the various aspects of the invention.

In a further preferred embodiment, the different probe sets in total selectively hybridize to at least the following genomic regions: 11p15.5 (pIGF2AP); 8p11.21 (SFRP1), and 9q32 (TNC).

The composition of each aspect and embodiment of the invention may further comprise other polynucleotide components that are beneficial for use in combination with the AML biomarker, such as competitor nucleic acids and other control sequences (such as sequences to provide a standard of hybridization for comparison, etc.) Such other polynucleotide components are not probe sets for purposes of the compositions and methods of the invention. The compositions may optionally comprise other components, including but not limited to buffer solutions, hybridization solutions, detectable labels, and reagents for storing the nucleic acid compositions.

As used herein with respect to each aspect and embodiment of the invention, the term "selectively hybridizes" means that the isolated polynucleotides bind to the particular genomic region or other target to form a hybridization complex, and minimally or not at all to other sequences. The specific hybridization conditions used will depend on the length of the polynucleotide probes employed, their GC content, as well as various other factors as is well known to those of skill in the art. (See, for example, Tijssen (1993) Laboratory Techniques in Biochemistry and Molecular Biology—Hybridization with Nucleic Acid Probes part I, chapter 2, "Overview of principles of hybridization and the strategy of nucleic acid probe assays," Elsevier, N.Y. ("Tijssen")). In one embodiment, stringent hybridization and wash conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. High stringency conditions are selected to be equal to the Tm for a particular probe. An example of stringent conditions are those that permit selective hybridization of the isolated polynucleotides to the genomic or other target nucleic acid to form hybridization complexes in 0.2×SSC at 65° C. for a desired period of time, and wash conditions of 0.2×SSC at 65° C. for 15 minutes. It is understood that these conditions may be duplicated using a variety of buffers and temperatures. SSC (see, e.g., Sambrook, Fritsch, and Maniatis, in: Molecular Cloning, A Laboratory Manual, Cold Spring Harbor Laboratory Press, 1989) is well known to those of skill in the art, as are other suitable hybridization buffers.

In each of the aspects and embodiments of the compositions and methods of the present invention, it is further preferred that the isolated polynucleotides are labeled with a detectable label. In a preferred embodiment, the detectable labels on the isolated polynucleotides in one probe set are all the same, and are distinguishable from the detectable labels on the isolated polynucleotides in the other probe sets in a given AML biomarker (i.e., the different probe sets are "differentially labeled"). Such labeling of the isolated polynucleotides facilitates differential determination of the signals from different reporter sets in a given AML biomarker. Useful detectable labels include but are not limited to radioactive labels such as $^{32}P$, $^{3}H$, and $^{14}C$; fluorescent dyes such as fluorescein isothiocyanate (FITC), rhodamine, lanthanide phosphors, Texas red, and ALEXA Fluor Dyes™ (Molecular Probes), CY™ dyes (Amersham), Spectrum Dyes (Abbott Labs); electron-dense reagents such as gold; enzymes such as horseradish peroxidase, beta-galactosidase, luciferase, and alkaline phosphatase; colorimetric labels such as colloidal gold; magnetic labels such as those sold under the mark DYNABEADS™; biotin; dioxigenin; or haptens and proteins for which antisera or monoclonal antibodies are available. The label can be directly incorporated into the polynucleotide, or it can be attached to a molecule which hybridizes or binds to the polynucleotide. The labels may be coupled to the isolated polynucleotides by any means known to those of skill in the art. In various embodiments, the isolated polynucleotides are labeled using nick translation, PCR, or random primer extension (see, e.g., Sambrook et al. supra). Methods for detecting the label include, but are not limited to spectroscopic, photochemical, biochemical, immunochemical, physical or chemical techniques.

Those of skill in the art are aware that multiple resources are available to identify specific nucleotide sequences associated with the genomic regions discussed above. In one example, such sequences can be found as follows:

Go to the UCSC web site, genome.ucsc.edu/index.html?org=Human. At this site, select the Genome Browser on the menu at the left. Then in the "position" field enter, (in this format, e.g. for chromosome 16p13): 16:11,000,000-12,000,000 and then select "jump" (position entries have to be either by gene name, clone name, accession number, etc. or base pair position, usually in millions) Once the image of the chromosome is in view, which has the base pairs at the top of the image, and the chromosome bands immediately below, the navigation tools can be used to zoom in or out, move to the left or right as necessary. To get to the sequence itself (for 16p13, as an example), select the band designation within the image, which leads to the "Chromosome Bands Localized by FISH Mapping Clones (p13.2)" page, which has the "View DNA for this feature" button. Choose the "View DNA . . . " button which leads to the "Get DNA in Window". At the bottom of that page choose the "Get DNA" button, and the sequence appears. At the very top of the sequence page the exact base pairs are shown.

Those of skill in the art will understand how to apply the present disclosure to identify the nucleotide sequences of other genomic regions of interest disclosed herein.

In a second aspect, the invention provides compositions comprising or consisting of an AML biomarker comprising or consisting of between 2 and 65 different probe sets, wherein at least 20% of the different probe sets comprise or consist of one or more isolated polynucleotides that selectively hybridize to a nucleic acid according to formula 1, or complements thereof:

X1-X2-X3;

wherein X2 is a human genomic insert contained within a bacterial artificial chromosome ("BAC") selected from the group consisting of SEQ ID NOS: 14-41 (see FIG. 1), wherein X1 and X3 are independently 0-500 kB of human genomic nucleic acid flanking X2 in the human genome; and wherein the different polynucleotide probe sets in total selectively hybridize to at least two non-overlapping polynucleotides according to formula 1, or complements thereof.

BAC sequence information is provided below in Table 1 (and as provided in FIG. 1).

TABLE 1

| (a) | TEAD1: | RP11-599L08 (SEQ ID NO: 14) |
| | | RP11-756C18 (SEQ ID NO: 15) |
| (b) | sGPX2 | RP11-101I03 (SEQ ID NO: 16) |
| (c) | COL3A1: | RP11-622E16 (SEQ ID NO: 17) |
| | | RP11-634B17 (SEQ ID NO: 18) |
| | | RP11-1151E08 (SEQ ID NO: 19) |
| (d) | EGFR: | RP11-781C22 (SEQ ID NO: 20) |
| | | CTD-2026N22 (SEQ ID NO: 21) |
| | | RP11-708P05 (SEQ ID NO: 22) |
| (e) | FBN1 | RP11-42K15 (SEQ ID NO: 23) |
| | | RP11-7J12 (SEQ ID NO: 24) |
| | | RP11-348A14 (SEQ ID NO: 25) |
| (f) | pIGF2AP | RP11-200C14 (SEQ ID NO: 26) |
| | | RP11-650O21 (SEQ ID NO: 27) |
| (g) | IL6ST | RP11-395G19 (SEQ ID NO: 28) |
| | | RP11-806P19 (SEQ ID NO: 29) |
| | | RP11-239D15 (SEQ ID NO: 30) |
| | | RP11-321M06 (SEQ ID NO: 31) |
| (h) | ITIH2 | RP11-454I03 (SEQ ID NO: 32) |
| | | RP11-45N19 (SEQ ID NO: 33) |
| (i) | NR2F2 | RP11-163P10 (SEQ ID NO: 34) |
| (j) | RAB25 | RP11-702H12 (SEQ ID NO: 35) |
| (k) | RGS10 | RP11-714M16 (SEQ ID NO: 36) |
| | | RP11-278I18 (SEQ ID NO: 37) |
| | | RP11-420N23 (SEQ ID NO: 38) |

TABLE 1-continued

| (l) | SFRP1 | RP11-11B23 (SEQ ID NO: 39) |
| (m) | TNC | RP11-818J03 (SEQ ID NO: 40) |
|  |  | RP11-472E10 (SEQ ID NO: 41) |

The nucleic acids disclosed above in the "X2" group are the human nucleic acids encompassing the marker genes (and portions of the genomic regions of the first aspect of the invention) discussed above, cloned into BAC vectors. (See FIG. 1) As will be apparent to those of skill in the art in reviewing FIG. 1, genomic regions for each of the cloned markers for AML prognosis described above (SEQ ID NO:1-13) are present in the BAC inserts listed within the "X2" groups above. For some of the 13 cloned markers, multiple overlapping BAC inserts are provided (see FIG. 1).

According to this second aspect of the invention, the different polynucleotide probe sets in total selectively hybridize to at least two non-overlapping nucleic acids according to Formula 1 (ie: at least two of (a)-(m) in Table 1).

In various preferred embodiments of this second aspect of the invention, the AML biomarker comprises or consists of 3, 4, 5, 6, 7, 8, 9, 10, 11, 12, or 13 different probe sets that selectively hybridize to a nucleic acid according to formula 1, or complements thereof. In each of these embodiments, it is further preferred that at least 30%, 40%, 50%, 60%, 70%, 80%, 90%, or 100% of the probe sets for a given AML biomarker comprise or consist of one or more isolated polynucleotides that selectively hybridize to a nucleic acid according to formula 1, or complements thereof, wherein the different polynucleotide probe sets in total selectively hybridize three non-overlapping nucleic acids according to formula 1.

In a further preferred embodiment of the second aspect of the invention, the different probe sets comprise or consist of one or more isolated polynucleotides that in total selectively hybridize to at least three different nucleic acids according to Formula I having X2 groups as follows:

a) one or more of SEQ ID NO:26-27 (includes pIGF2AP), or complements thereof;

b) one or more of SEQ ID NO:40-41(includes TNC), or complements thereof; and c) SEQ ID NO: 39 (includes SFRP1), or complements thereof.

As will be apparent to those of skill in the art, as the percentage of probe sets that comprise or consist of one or more isolated polynucleotides that selectively hybridize to a nucleic acid sequence according to formula 1, or its complement, the maximum number of probe sets in the AML biomarker will decrease accordingly. Thus, for example, where at least 50% of the probe sets comprise or consist of one or more isolated polynucleotides that selectively hybridize to a nucleic acid sequence according to formula 1, or its complement, the AML marker will consist of between 2 and 26 probe sets. Those of skill in the art will recognize the various other permutations encompassed by the compositions according to the various embodiments of the second aspect of the invention.

In a further preferred embodiment of each of the above embodiments of the second aspect of the invention, X1 and X3 are 0-400 kb, 0-300 kb, 0-200 kb, 0-100 kb, or 0 kb.

In a preferred embodiment of the various embodiments of the second aspect of the invention, the different probe sets of an AML biomarker comprise or consist of one or more polynucleotide sequences of at least 10 nucleotides of a nucleic acid according to formula 1, or its complement. In a further preferred embodiment, the different probe sets of a AML biomarker comprise or consist of one or more polynucleotides of at least 10 nucleotides of a nucleic acid selected from the group consisting of SEQ ID NOS:14-41 or complements thereof.

In various further preferred embodiments of each of the embodiments of the first and second aspects of the invention, and related aspects and embodiments described below, the polynucleotides in the probe set independently comprise or consist of at least 10, 15, 20, 25,30, 35, 40, 45, 50, 55, 60, 65, 70, 75, 80, 85, 90, 95,100, 150, 200, 250, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, 9900, 10,000; 15,000; 20,000; 25,000; 30, 000; 35,000; 40,0000; 45,000; 50,000; 60,000; 70,000; 80,000; 90,000; 100,000; 110,000; 120,000; 130,000; 140,000; 150,000; 160,000; 170,000; 180, 000; 190,000; 200,000; 210,000; or 220,000 nucleotides of the relevant sequence.

The BACS disclosed herein are as defined on the University of California at Santa Cruz (UCSC) Genome Browser on Human April 2003 Freeze and are available from the Children's Hospital Oakland Research Institute at web site bacpac.chori.org. The human genomic inserts cloned into the BACS disclosed herein range in size from approximately 150 kB to 220 in length.

As of March of 2004, detailed information on the BACS is available by going to the web site for the Children's Hospital Oakland Research Institute at web site bacpac.chori.org and clicking on the link to "Human '32K' BAC Re-array" under the products menu. From this page, web site bcgsc.ca/lab/mapping/bacrearray/human/ provides a link to the Genome Sciences Centre web page. From this page, go to the Annotations box and find the further box for "Browse clone set". Within that box is a link to the UCSC Genome Browser; click on the link that says "available," which takes you to web site genome.ucsc.edu/cgi-bin/hgTracks, where detailed BAC information, such as that provided in the accompanying figures, can be found. The BACS can be found by searching by BAC name or by gene name. The sequence of the human genomic insert cloned in a BAC of interest can be found at web site genome.ucsc.edu/cgi-bin/hgTracks. Once the BAC of interest has been found in the database, as described above, the sequence of each BAC be found by "clicking" on the name of the BAC. The first click connects to a "Custom Track" for that BAC. On the Custom Track page there is an option called "View DNA for this feature", which is a link to the "Get DNA" window, for that specific BAC. On the "Get DNA" page, the "Get DNA" button retrieves the complete DNA sequence for that BAC clone. Furthermore, sequences flanking the BAC of interest can also be retrieved from the "Get DNA" page by using "Sequence Retrieval Option": the number of bases desired both upstream and downstream of the BAC are entered and, and those flanking sequences are then retrieved along with the sequence of the BAC itself. Furthermore, the detailed information on the BACS provided herein discloses the genomic location in terms of base pair position of the human genomic insert cloned in BACS as of the Human April 2003 Freeze.

As will be understood by those of skill in the art, the human genome sequence is frequently updated, with the updates made available to the public. Those of skill in the art will thus be able to identify the sequences flanking the human genomic insert cloned in a BAC of interest disclosed herein by accessing the human genome information (for example, at web site genome.ucsc.edu/). Therefore, the "flanking sequences" as recited herein refer to flanking sequences as disclosed on the web sites provided above, as well as updates thereto. For example, one can go to the UCSC Genome Browser site as disclosed above and review the BAC information as of the Human April 2003 Freeze to get the relative base pair position on the chromosome that the human genomic insert cloned in a BAC of interest was derived from. By reviewing the human genome sequence data available at as of the Human April 2003 Freeze (as described above), one of skill in the art can obtain the nucleic acid sequences flanking the human genomic insert cloned in a BAC of interest disclosed herein. Those of skill in the art can further use this sequence to identify sequences flanking the human genomic insert cloned in a BAC of interest from this same site as currently updated in the human genome sequence, or from other similar sites that provide human genome sequence information.

In a third aspect, the present invention provides compositions comprising or consisting of an AML biomarker comprising or consisting of between 2 and 65 different probe sets, wherein at least 20% of the different probe sets comprise or consist of one or more isolated polynucleotides that selectively hybridize to a nucleic acid sequence according to one of SEQ ID NOS:1-13 or complements thereof; wherein the different probe sets in total selectively hybridize to at least two of the recited nucleic acid sequences according to SEQ ID NOS: 1-13 or complements thereof.

In various preferred embodiments of the third aspect of the invention, the composition comprises or consists of an AML biomarker comprising or consisting of 3, 4, 5, 6, 7, 8, 9, 10, 11, 12, or 13 different probe sets that selectively hybridize to a nucleic acid according to one of SEQ ID NOS:1-13 or complements thereof, wherein the different probe sets in total selectively hybridize to 3, 4, 5, 6, 7, 8, 9, 10, 11, 12, or 13 of the nucleic acid sequences according to SEQ ID NOS:1-13 or complements thereof. In each of these embodiments, it is further preferred that at least 30%, 40%, 50%, 60%, 70%, 80%, 90%, or 100% of the probe sets for a given AML biomarker comprise or consist of one or more isolated polynucleotides that selectively hybridize to a nucleic acid according to SEQ ID NOS:1-13, or complements thereof. As will be apparent to those of skill in the art, as the percentage of probe sets that comprise or consist of one or more isolated polynucleotides that selectively hybridize to a nucleic acid according to SEQ ID NOS:1-13, or complements thereof, the maximum number of probe sets in the AML biomarker will decrease accordingly. Thus, for example, where at least 50% of the probe sets comprise or consist of one or more isolated polynucleotides that selectively hybridize to a nucleic acid according to SEQ ID NOS:1-13, or complements thereof, the AML marker will consist of between 2 and 26 probe sets. Those of skill in the art will recognize the various other permutations encompassed by the compositions according to the various embodiments of the third aspect of the invention.

In a preferred embodiment of the various embodiments of the third aspect of the invention, the different probe sets of a AML biomarker comprise or consist of one or more polynucleotides of at least 10 nucleotides of a nucleic acid according to SEQ ID NOS:1-13, or complements thereof.

In a further preferred embodiment, the different probe sets comprise or consist of isolated polynucleotides that in total selectively hybridize to at least SEQ ID NOS:6, 12 and 13, or complements thereof. In this embodiment, it is further preferred that at least 25%, 30%, 35%, 40%, 45%, 50%, 55%, 60%, 65%, 70%, 80%, 85%, 90% 95% or 100% of the probe sets comprise or consist of one or more isolated polynucleotides that selectively hybridize to one of these recited nucleic acids, or complements thereof.

The compositions of this third aspect of the invention are especially preferred for analysis of RNA expression from the genes in a tissue of interest, such as peripheral blood, granulocyte precursors, monocyte precursors, inflammatory sites, or bone marrow samples from an AML patient. Such polynucleotides according to this aspect of the invention can be of any length that permits selective hybridization to the nucleic acid of interest. In various preferred embodiments of the third aspect of the invention and related aspects and embodiments disclosed below, the isolated polynucleotides comprise or consist of at least 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, or 1000 nucleotides according to a nucleic acid sequence selected from the group consisting of SEQ ID NOS:1-13 or complements thereof. In further embodiments, an isolated polynucleotide according to this third aspect of the invention comprise or consist of a nucleic acid sequence according to one of SEQ ID NOS:1-13 or complements thereof.

The compositions of the various aspects and embodiments of the invention can be in lyophilized form, or preferably comprise a solution containing the isolated polynucleotides or polypeptides, including but not limited to buffer solutions, hybridization solutions, and solutions for keeping the compositions in storage. Such a solution can be made as such, or the composition can be prepared at the time of hybridizing the polynucleotides to a target sequence as discussed below.

Alternatively, the compositions can be placed on a solid support, such as in a microarray, bead, or microplate format. The term "microarray" as used herein refers to a plurality of probe sets immobilized on a solid surface to which sample nucleic acids are hybridized (such as mRNA or derived cDNA from an AML patient) are bound.

Thus, in a fourth aspect, the present invention provides microarrays comprising a support structure on which are arrayed probe sets according to the compositions of the invention, as disclosed above. In this aspect, a single probe set can be present at a single location on the array, or different polynucleotides from a single probe set can be present at different and defined locations on the array.

In this aspect, the polynucleotides or polypeptides are immobilized on a microarray solid surface. Other nucleic acid sequences, such as reference or control nucleic acids, can be optionally immobilized on the solid surface as well. Methods for immobilizing nucleic acids on a variety of solid surfaces are well known to those of skill in the art. A wide variety of materials can be used for the solid surface. Examples of such solid surface materials include, but are not limited to, nitrocellulose, nylon, glass, quartz, diazotized membranes (paper or nylon), silicones, polyformaldehyde, cellulose, cellulose acetate, paper, ceramics, metals, metalloids, semiconductive materials, coated beads, magnetic particles; plastics such as polyethylene, polypropylene, and polystyrene; and gel-forming materials, such as proteins (e.g., gelatins), lipopolysaccharides, silicates, agarose and polyacrylamides.

A variety of different materials may be used to prepare the microarray solid surface to obtain various properties. For example, proteins (e.g., bovine serum albumin) or mixtures of macromolecules (e.g., Denhardt's solution) can be used to minimize non-specific binding, simplify covalent conjugation, and/or enhance signal detection. If covalent bonding between a compound and the surface is desired, the surface will usually be functionalized or capable of being functionalized. Functional groups which may be present on the surface and used for linking include, but are not limited to, carboxylic acids, aldehydes, amino groups, cyano groups, ethylenic groups, hydroxyl groups, and mercapto groups. Methods for linking a wide variety of compounds to various solid surfaces are well known to those of skill in the art.

In a preferred embodiment of this aspect, the locations on the array containing probe sets of the present invention range in size between 1 μm and 1 cm in diameter, more preferably between 1 μm and 5 mm in diameter, and even more preferably between 5 μm and 1 mm in diameter. The polynucleotides of the probe sets may be arranged on the solid surface at different densities, depending on factors such as the nature of the label, the solid support, and the size of the polynucleotide. One of skill will recognize that each location on the microarray may comprise a mixture of polynucleotides of different lengths and sequences from a given probe set. The length and complexity of the polynucleotides fixed onto the locations can be adjusted to provide optimum hybridization/binding and signal production for a given hybridization/binding procedure, and to provide the required resolution.

In a fifth aspect, the present invention provides methods for classifying AML in a patient, comprising
  (a) contacting a nucleic acid sample obtained from a subject having AML with polynucleotide probes that, in total, selectively hybridize to two or more genomic regions selected from the group consisting of 11p15.2; 5q11.2; 2q32.2; 7p11.2; 15q21.1; 11p15.5; 10p14; 15q26.2; 1q22; 10q26.11; 8p11.21; and 9q32; wherein the contacting occurs under conditions to promote selective hybridization of the polynucleotides of the probe set to the two or more genomic regions;
  (b) detecting formation of hybridization complexes;
  (c) determining whether one or more of the genomic regions are present in an altered copy number in the nucleic acid sample; and
  (d) correlating an altered copy number of one or more of the genomic regions with an AML classification.

The nucleic acid sample used in the methods of the present invention can be from any source useful in providing a prognosis for an AML patient, including but not limited to peripheral blood, inflammatory sites, or bone marrow sample from a human AML patient, or in specific cells isolated from such specimens, such as granulocyte precursors, or monocyte precursors. The nucleic acid sample is preferably a cellular DNA sample. In a preferred embodiment, the nucleic acid sample is a human nucleic acid sample.

In a preferred embodiment of this aspect of the invention, the method further comprises identifying the AML patient as being of the normal karyotype subclass prior to or simultaneously with carrying out steps (a)-(d). As used herein, "normal karyotype subclass" means that the AML patient does not possess any of the genetic abnormalities often associated with AML, including t(8;21), t(15;17), inv(16), t(9;11), inv(3), −5/del(5q), and −7/del(7q), t(6;9), or abnormalities involving 11q23. Thus, in this embodiment, the method is carried out simultaneously with or following a karyotype analysis for the AML patient that does not show any AML-correlated karyotype abnormalities. As used herein, "following" includes immediately following, or following at some future time.

In a further embodiment of any of the above embodiments, the method may further comprise determining the AML morphological subtype, as described above.

In the fifth aspect of the invention the methods are used to detect genomic amplifications or deletions associated with AML. As used herein "associated with AML" means that an altered copy number of one or more of these genomic regions can be used to provide a prognosis of a patient from whom the nucleic acid sample was taken, including the following:
  (a) Patient prognosis in the absence of therapy (ie: chemotherapy or radiation therapy);
  (b) Prognosis of patient response to treatment (chemotherapy, radiation therapy);
  (c) Predicted optimal course of treatment for the patient;
  (d) Prognosis for patient relapse after treatment, for example, by prognosis of minimal residual disease (such patients have high risk of relapse); and/or
  (e) Patient life expectancy.

Thus, the methods of this aspect of the invention provide information on AML patient prognosis in the presence or absence of treatment, a predicted optimal course for treatment of the patient, and patient life expectancy. In a further preferred embodiment, an alteration (ie: increase or decrease) in the copy number of the one or more genomic regions is correlated with an increased risk of recurrence of AML. In a most preferred embodiment, a decrease in copy number of the one or more genomic regions is correlated with a higher risk of poor outcome. This decrease can be an absolute decrease in copy number of the genomic region(s) to less than two, or can be a decrease relative to those AML patients with a good prognosis.

As used herein, "poor outcome" means relapse, death due to disease, shorter disease-free survival, and shorter event-free survival.

As used herein, "disease free survival (DFS)" means the period without any evidence of the original disease. "Shorter DFS" means, by comparison to the "good outcome" group, the duration of DFS is statistically significantly decreased.

As used herein, "event" means incomplete remission, relapse, or death during a first complete remission". "Event free survival (EFS)" means the period without any event. "Shorter EFS" means, by comparison to the "good outcome" group, the duration of EFS is statistically significantly decreased.

As used herein, "relapse" means that, at some point after the patient has achieved remission, AML recurs.

As used herein for all aspects and embodiments of the methods, an "alteration in copy number" means any increase or decrease in copy number of the genomic region or target relative to the copy number in a normal diploid human genome. It is understand that for most expressed genes in the human genome this normal number will be two.

Thus, the invention further provides methods for making a treatment decision for an AML patient, comprising carrying out the methods for classifying AML according to the different aspects and embodiments of the present invention, and then weighing the results in light of other known clinical and pathological risk factors, in determining a course of treatment for the AML patient.

In various preferred embodiments of the methods of the fifth aspect of the invention, the compositions are selected from the various aspects and embodiments of the compositions of the invention disclosed above. In a most preferred embodiment, the polynucleotides of the probe sets comprise a detectable label, as disclosed above, and in particular the different probe sets comprise distinguishable detectable labels, to facilitate analysis of which genomic region(s) is/are the site of the an altered copy number.

In a sixth aspect, the present invention provides methods for classifying AML comprising:
  (a) contacting a mRNA-derived nucleic acid sample obtained from a subject having AML with nucleic acid probes that, in total, selectively hybridize to two or more nucleic acid targets selected from the group consisting of SEQ ID NO:1-13 or complements thereof; wherein the contacting occurs under conditions to promote selective hybridization of the nucleic acid probes to the nucleic acid targets, or complements thereof, present in the nucleic acid sample;

(b) detecting formation of hybridization complexes between the nucleic acid probes to the nucleic acid targets, or complements thereof, wherein a number of such hybridization complexes provides a measure of gene expression of the one or more nucleic acids according to SEQ ID NO:1-13; and (c) correlating an alteration in gene expression (ie, an increase or decrease) of the one or more nucleic acids according to SEQ ID NO:1-13 relative to control with an AML classification. In a preferred embodiment, the classification comprises AML recurrence.

The method according to the sixth aspect of the invention detects alterations in gene expression of one or more of the markers according to SEQ ID NO:1-13 relative to a control with a modification in expression relative to control correlating with a classification of the AML as likely to recur.

In the sixth aspect of the invention the methods are used to detect gene expression alterations associated with AML. As used herein "associated with AML" means that an altered expression level of one or more of the markers can be used to classify a feature of the AML or the prognosis of a patient from whom the nucleic acid sample was taken.

Any control known in the art can be used in the methods of the invention. For example, the expression level of a gene known to be expressed at a relatively constant level in both AML and non-AML samples can be used for comparison. Alternatively, the expression level of the genes targeted by the probes can be analyzed in non-AML RNA samples equivalent to the test sample. Those of skill in the art will recognize that many such controls can be used in the methods of the invention.

In a preferred embodiment of this sixth aspect of the invention, the method further comprises identifying the AML patient as being of the normal karyotype subclass prior to or simultaneously with carrying out steps (a)-(c). As used herein, "normal karyotype subclass" means that the AML patient does not possess any of the genetic abnormalities often associated with AML, including t(8;21), t(15;17), inv (16), t(9;11), inv(3), −5/del(5q), t(6;9), −7/del(7q), t(9;22) or abnormalities involving 11q23. Thus, in this embodiment, the method is carried out simultaneously with or following a karyotype analysis for the AML patient that does not show any AML-correlated karyotype abnormalities. As used herein, "following" includes immediately following, or following at some future time.

In a further embodiment of any of the above embodiments, the method may further comprise determining the AML morphological subtype, as described above.

In the sixth aspect of the invention the methods are used to detect gene expression changes associated with AML. As used herein "associated with AML" means that an expression level of one or more of these marker genes can be used to provide a prognosis of an AML patient from whom the nucleic acid sample was taken, including the following:

(a) Patient prognosis in the absence of therapy (ie: chemotherapy or radiation therapy;

(b) Prognosis of patient response to treatment (chemotherapy, radiation therapy)

(c) Predicted optimal course of treatment for the patient;

(d) Prognosis for patient relapse after treatment, for example, by prognosis of minimal residual disease (such patients have high risk of relapse)

(e) Patient life expectancy.

In a further preferred embodiment, an alteration (ie: increase or decrease) in the expression level of the one or more nucleic acid targets is correlated with an increased risk of recurrence of AML. In a most preferred embodiment, a decrease in expression level of the one or more nucleic acid targets is correlated with a higher risk of poor outcome, as defined above. This decrease can be an absolute decrease in expression of the nucleic acid markers relative to control, or can be a decrease relative to those AML patients with a good prognosis.

Thus, the methods of this aspect of the invention provide information on, for example, AML patient prognosis in the presence or absence of chemotherapy, a predicted optimal course for treatment of the patient, and patient life expectancy.

Thus, the invention further provides methods for making a treatment decision for an AML patient, comprising carrying out the methods for classifying an AML according to the different aspects and embodiments of the present invention, and then weighing the results in light of other known clinical and pathological risk factors, in determining a course of treatment for the AML patient. For example, a patient that is shown by the methods of the invention to have an increased risk of poor outcome could be treated more aggressively with standard therapies, such as chemotherapy, radiation therapy, and/or bone marrow transplant The mRNA-derived nucleic acid sample used in the methods of the present invention can be mRNA or cDNA derived from the mRNA. The RNA sample used in the methods of the present invention can be from any source useful in providing a prognosis on an AML patient, including but not limited to peripheral blood, inflammatory sites, or bone marrow sample from a human AML patient, or in specific cells isolated from such specimens, such as granulocyte precursors, or monocyte precursors. The nucleic acid sample is preferably a cellular DNA or RNA sample, such as a sample prepared for in situ hybridization.

In various preferred embodiments of the methods of the sixth aspect of the invention, the nucleic acid probes are selected from the various aspects and embodiments of the compositions disclosed above, particularly the third aspect of the invention and preferred embodiments thereof In a most preferred embodiment, the polynucleotides of the probe sets comprise a detectable label, as disclosed above, and in particular the different probe sets comprise distinguishable detectable labels, to facilitate analysis of changes in marker gene expression.

In a most preferred embodiment of this aspect, the nucleic acid probes comprise or consist of single stranded anti-sense polynucleotides of the nucleic acid compositions of the invention. For example, in mRNA fluorescence in situ hybridization (FISH) (ie. FISH to detect messenger RNA), only an anti-sense probe strand hybridizes to the single stranded mRNA in the RNA sample, and in that embodiment, the "sense" strand oligonucleotide can be used as a negative control.

Alternatively, DNA probes can be used as probes, preferably those according to the compositions of the invention. In this embodiment, it is preferable to distinguish between hybridization to cytoplasmic RNA and hybridization to nuclear DNA. There are two major criteria for making this distinction: (1) copy number differences between the types of targets (hundreds to thousands of copies of RNA vs. two copies of DNA) which will normally create significant differences in signal intensities and (2) clear morphological distinction between the cytoplasm (where hybridization to RNA targets would occur) and the nucleus will make signal location unambiguous. Thus, when using double stranded DNA probes, it is preferred that the method further comprises distinguishing the cytoplasm and nucleus in cells being analyzed within the bodily fluid sample. Such distinguishing can be accomplished by any means known in the art, such as by using a nuclear stain such as Hoechst 33342, or DAPI which delineate the nuclear DNA in the cells being analyzed. In this embodiment, it is preferred that the nuclear stain is distinguishable from the detectable probes. It is further preferred that the nuclear membrane be maintained, i.e., that all the Hoechst or DAPI stain be maintained in the visible structure of the nucleus.

Any conditions, including hybridization reagents and wash conditions to remove unbound probe, in which the nucleic acid probes bind selectively to the target in the nucleic acid sample in the nucleic acid sample to form a hybridization complex, and minimally or not at all to other sequences, can be used in the methods of the present invention, as discussed above. Further optional steps can include, but are not limited to, pre-hybridization of the nucleic acid sample and use of competitor nucleic acids. For example, such hybridization conditions may include (1) fixation of tissue, biological structure, or nucleic acid sample to be analyzed; (2) pre-hybridization treatment of the tissue, biological structure, or nucleic acid sample to increase accessibility of the nucleic acid sample (within the tissue or biological structure in those embodiments), and to reduce nonspecific binding; (3) hybridization of the probe to the nucleic acid sample; (4) post-hybridization washes to remove probe not bound in the hybridization and (5) detection of the hybridized nucleic acid fragments.

Any method for detecting formation of hybridization complexes and determining an alteration in marker gene expression can be used (including quantitative or semi-quantitative methods), including but not limited to in situ hybridization (such as fluorescent in situ hybridization (FISH)), polymerase chain reaction (PCR) analysis, reverse transcription polymerase chain reaction (RT-PCR) analysis, Real Time PCR, Taq Man PCR, Southern blotting, Northern blotting, array-based methods, and/or comparative genomic hybridization.

In a preferred embodiment, detection is performed by in situ hybridization ("ISH"). In situ hybridization assays are well known to those of skill in the art. Generally, in situ hybridization comprises the following major steps (see, for example, U.S. Pat. No. 6,664,057): (1) fixation of tissue, biological structure, or nucleic acid sample to be analyzed; (2) pre-hybridization treatment of the tissue, biological structure, or nucleic acid sample to increase accessibility of the nucleic acid sample (within the tissue or biological structure in those embodiments), and to reduce nonspecific binding; (3) hybridization of the probe to the nucleic acid sample; (4) post-hybridization washes to remove probe not bound in the hybridization and (5) detection of the hybridized nucleic acid fragments. The reagent used in each of these steps and their conditions for use varies depending on the particular application. In a particularly preferred embodiment, ISH is conducted according to methods disclosed in U.S. Pat. Nos. 5,750,340 and/or 6,022,689, incorporated by reference herein in their entirety.

In a typical in situ hybridization assay, cells are fixed to a solid support, typically a glass slide. The cells are typically denatured with heat or alkali and then contacted with a hybridization solution to permit annealing of labeled probes specific to the target nucleic acid sequence. The polynucleotides of the invention are typically labeled, as discussed above. In some applications it is necessary to block the hybridization capacity of repetitive sequences. In this case, human genomic DNA or Cot-1 DNA is used to block non-specific hybridization.

In a further embodiment, an array-based format can be used in which the polynucleotides of the invention can be arrayed on a surface and the human nucleic sample is hybridized to the polynucleotides on the surface. In this type of format, large number of different hybridization reactions can be run essentially "in parallel." This provides rapid, essentially simultaneous, evaluation of a large number of nucleic acid probes. Methods of performing hybridization reactions in array based formats are also described in, for example, Pastinen (1997) Genome Res. 7:606-614; (1997) Jackson (1996) Nature Biotechnology 14:1685; Chee (1995) Science 274:610; WO 96/17958. Methods for immobilizing the polynucleotides on the surface and derivatizing the surface are known in the art; see, for example, U.S. Pat. No. 6,664,057, and are also described above.

In each of the above aspects and embodiments, detection of hybridization is typically accomplished through the use of a detectable label on the nucleic acid probes, such as those described above. The label can be directly incorporated into the polynucleotide, or it can be attached to a molecule which hybridizes or binds to the polynucleotide. The labels may be coupled to the probes in a variety of means known to those of skill in the art, as described above. In a preferred embodiment, the detectable labels on the different probe sets of the compositions of the invention are distinguishable from each other, as discussed above. The label can be detectable can be by any techniques, including but not limited to spectroscopic, photochemical, biochemical, immunochemical, physical or chemical techniques, as discussed above.

In a further aspect, the present invention provides kits for use in the methods of the invention, comprising the compositions of the invention and instructions for their use. In a preferred embodiment, the probe sets are labeled, preferably so as to distinguish different probe sets, as disclosed above. In a further preferred embodiment, the probe sets are provided in solution, most preferably in a hybridization buffer to be used in the methods of the invention. In a further embodiment, the probe sets are provided on a solid support, such as those described above. In further embodiments, the kit also comprises wash solutions and/or pre-hybridization solutions.

EXAMPLES

Gene Expression Prognosis Markers for Normal Karyotype Adult AML Patients.

Certain chromosomal abnormalities are routinely used to determine prognosis in adult AML patients. However a significant proportion of these patients do not exhibit such abnormalities. These patients are termed the normal karyotype subset of AML patients. A gene expression signature indicative of prognosis in these patients would likely be of great clinical utility for these patients. We have identified and validated several two-gene and three-gene signatures correlating with prognosis in a publicly available gene expression dataset (See FIG. 2).

Source of gene expression data: NCBI Gene Expression Omnibus (GEO) GSE425

Supporting paper: Bullinger L, Dohner K, Bair E, Frohling S, Schlenk R F, Tibshirani R, Dohner H, Pollack J R. Use of gene-expression profiling to identify prognostic subclasses in adult acute myeloid leukemia. N Engl J Med. 2004 Apr 15;350(16):1605-16.

The gene expression data consists of 6285 gene expression measurements for each of 45 peripheral blood and bone marrow samples collected from patients with normal karyotype as determined from standard cytogenetic testing. In this group, 31 patients who had died (mean time to death 277 days) from their disease were defined as having a poor outcome, and 14 patients who were alive at last available follow-up (mean follow-up 540 days) were defined as having a good outcome.

Approximately 75% of the samples were randomly selected for marker discovery, and the remaining 25% was used for testing the discovered markers.

Prognostic two and three gene combinations were sought using a proprietary technique that could distinguish the good and poor prognosis patients. 191 three gene combinations were identified. The statistical significance of these combinations was computed using a label permutation technique, and 42 of these were found to be significant at p=0.05. The independent test set classification results are presented in FIG. 2; thirteen genes are represented in the 42 prognostic combinations. Each of rows 4-45 reports the results for one particular 3 gene marker using the genes (clones) in the first three columns. The columns are divided into three groups: training results, bootstrap results, and results on 'blinded' withheld test data.

The training results are the results of finding a marker within the training data, and then determining the accuracy of the marker within that same data.

The bootstrap results are actually training results as well, but computed using a much more computationally expensive approach to marker accuracy estimation.

The test results are computed by applying the marker found using only the training data to the withheld test data.

Each of these three results are reported as: # of poor outcome samples misclassified, total poor outcome samples, # good outcome samples misclassified, total # good outcome samples. There are a total of 45 samples represented in the data. Looking at the training data and test data results: 45 samples=23 poor outcome training samples+10 good outcome training samples+8 poor outcome test samples+4 good outcome test samples.

The bootstrap approach repeatedly uses the training samples in the estimation process. The reported numbers are cumulative, and thus the total good (poor) samples are much larger than the actual number, and since these are the same training samples, these numbers don't appear in the sum above.

Top three-gene marker: pIGF2AP, TNC, SFRP1

Training Set:

| Prognosis | Alive | Dead |
|---|---|---|
| Good | 10 | 7 |
| Poor | 0 | 16 |

Bootstrap:

| Prognosis | Alive | Dead |
|---|---|---|
| Good | 351 | 303 |
| Poor | 55 | 691 |

Test Set:

| Prognosis | Alive | Dead |
|---|---|---|
| Good | 4 | 0 |
| Poor | 0 | 8 |

Training set accuracy: 79%

Bootstrap accuracy: 74%

Test set accuracy: 100%

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07557198B2). An electronic copy of the "Sequence Listing" will also be available from the USPTO upon request and payment of the fee set forth in 37 CFR 1.19(b)(3).

We claim:

1. An AML biomarker consisting of between 3 and 65 different probe sets, wherein at least 20% of the different probe sets consist of one or more isolated polynucleotides of 20 or more contiguous nucleotides of one of SEQ ID NOS: 1-13 or 20 or more contiguous nucleotides fully complementary to one of SEQ ID NOS:1-13; wherein a first probe set consists of one or more isolated polynucleotides of 1000 or more contiguous nucleotides of SEQ ID NO:6 or 1000 or more contiguous nucleotides fully complementary to SEQ ID NO:6; wherein a second probe set consists of one or more isolated polynucleotides of 1000 or more contiguous nucleotides of SEQ ID NO:12 or 1000 or more contiguous nucleotides fully complementary to SEQ ID NO:12; and wherein a third probe set consists of one or more isolated polynucleotides of 1000 or more contiguous nucleotides of SEQ ID NO:13 or 1000 or more contiguous nucleotides fully complementary to SEQ ID NO:13.

2. The AML biomarker of claim 1 wherein at least 50% of the different probe sets consist of 20 or more contiguous nucleotides of one of SEQ ID NOS:1-13 or 20 or more contiguous nucleotides fully complementary to one of SEQ ID NOS:1-13.

3. The AML biomarker of claim 1 wherein at least 70% of the different probe sets consist of 20 or more contiguous nucleotides of one of SEQ ID NOS:1-13 or 20 or more contiguous nucleotides fully complementary to one of SEQ ID NOS:1-13.

4. The AML biomarker of claim 1 wherein at least 80% of the different probe sets consist of 20 or more contiguous nucleotides of one of SEQ ID NOS:1-13 or 20 or more contiguous nucleotides fully complementary to one of SEQ ID NOS:1-13.

5. The AML biomarker of claim 1 wherein at least 90% of the different probe sets consist of 20 or more contiguous nucleotides of one of SEQ ID NOS:1-13 or 20 or more contiguous nucleotides fully complementary to one of SEQ ID NOS:1-13.

6. The AML biomarker of claim 1 wherein the one or more isolated polynucleotides of 20 or more contiguous nucleotides of one of SEQ ID NOS:1-13 or 20 or more contiguous nucleotides fully complementary to one of SEQ ID NOS:1-13 are detectably labeled.

7. The AML biomarker of claim 6 wherein the detectable label is a fluorescent dye.

8. The AML biomarker of claim 1, wherein the one or more isolated polynucleotides of 20 or more contiguous nucleotides of one of SEQ ID NOS:1-13 or 20 or more contiguous nucleotides fully complementary to one of SEQ ID NOS:1-13 comprise DNA.

9. The AML biomarker of claim 8, wherein the DNA is single stranded DNA.

10. The AML biomarker of claim 8, wherein the DNA is double stranded DNA.

* * * * *